United States Patent [19]
Russo

[11] 3,964,163
[45] June 22, 1976

[54] SURGICAL SAW BLADE FASTENING MEANS

[75] Inventor: Anthony Russo, La Habra, Calif.

[73] Assignee: Minnesota Mining and Manufacturing Company, St. Paul, Minn.

[22] Filed: Sept. 4, 1975

[21] Appl. No.: 610,100

[52] U.S. Cl. ............................. 30/166 R; 30/342; 83/698; 83/697; 279/42; 279/101; 128/317
[51] Int. Cl.² ................. B26D 1/06; A61B 17/14; B23D 49/10
[58] Field of Search ............ 83/698, 697; 279/42, 279/101; 30/166, 342, 392; 128/317

[56] References Cited
UNITED STATES PATENTS

| | | | |
|---|---|---|---|
| 2,689,131 | 9/1954 | Priest | 279/101 |
| 3,041,724 | 7/1962 | Bobkowski | 279/101 X |

Primary Examiner—Willie G. Abercrombie
Attorney, Agent, or Firm—Alexander, Sell, Steldt & DeLaHunt

[57] ABSTRACT

A surgical saw blade fastening means comprising a saw blade and chuck wich provides for positive locking of the blade while permitting rapid removal of the saw blade without the use of additional tools is disclosed. The chuck which is provided with an adapter portion so it can be attached to surgical instruments presently in use comprises a slotted body portion having a pyramid locator at the base of the slots into which the notched end of a saw blade is seated by the action of a knurled internally threaded collar carried on said chuck body in cooperation with the teeth of the saw blade.

5 Claims, 2 Drawing Figures

SURGICAL SAW BLADE FASTENING MEANS

BACKGROUND OF THE INVENTION

The present invention relates to a surgical saw blade fastening means and more specifically to a combination of a saw blade and chuck assembly for use on a powered reciprocating surgical instrument.

Prior art surgical saw blades have almost universally consisted of a shank portion and a blade portion formed from separate stock and secured to the shank portion by suitable means such as by brazing. The shank portion of such blades have usually been cylindrical with a flat provided thereon for locking engagement by a set-screw on the surgical instrument into which the shank is inserted. Replacement of such blades, of course, requires that the set-screw be loosened to permit the shank to be withdrawn. Also, discarding of such blades when dulled meant that the shank was also discarded.

U.S. Pat. No. 2,951,482, issued Sept. 6, 1960, discloses a surgical saw blade for a hand saw having a generally rectangularly shaped shank portion which fits into a slotted stem of a chuck and is clamped therein by the action of a threaded collar being threaded onto the bifurcated stem.

U.S. Pat. No. 3,041,724, issued July 3, 1962, relates to a hand extension tool for non-surgical uses and comprises a plurality of elongated tool elements divided by transverse score lines so that when a working surface such as a knife edge has been worn it can be broken off and a new working surface exposed. The upper longitudinal edge of the tool elements is threaded over its entire length and the opposite (lower) longitudinal edge is threaded at spaced locations along its length with working surfaces provided between the threaded portions. The threads are engaged by a nut rotatably mounted within one end of the handle. The tool element is prevented from rotation within the handle by a slotted cylindrical member fixed to the handle.

Although the foregoing patents show that prior workers have not been unaware of the desirability of having a tool wherein blades could be changed without the use of additional tools, so far as is known, no one has addressed the problem as it relates to a powered reciprocating instrument and particularly a surgical instrument for use on living bone and its attendant critical requirements.

SUMMARY OF THE INVENTION

The surgical saw blade fastening means of the present invention comprises a combination of a surgical saw blade and a chuck assembly providing for quick and simple yet positive attachment of the saw blade to the power source without the use of additional tools.

A typical power source for a surgical saw reciprocates the saw blade at a frequency of approximately 20,000 reciprocations per minute with a stroke of about 0.10 inch. It is, therefore, imperative that the blade be securely held in place to prevent wobbling and levering of the blade during use. Any degree of wobbling would be greatly aggravated by the short rapid reciprocating action of the power source and such wobbling would be particularly intolerable in a surgical procedure involving living bone and surrounding tissue.

The surgical saw blade of the present invention which is used for sectioning bone in a surgical procedure is greatly simplified when compared to those of the prior art and comprises a relatively thin planar blade member having a plurality of cutting teeth formed on an edge of said blade member, the other edge of the blade member being curved adjacent one end thereof to form a generally pointed relatively blunt front or leading end. The rear or trailing end of the blade is provided with locating and locking means in the form of a V-shaped notch which, in cooperation with the chuck assembly, securely attaches the blade to a suitable power source.

The chuck assembly comprises a shank portion adapted for attachment to a surgical instrument in the conventional manner and a body portion provided with at least one axial slot therein to accept the rear or trailing end of the saw blade therein. The base of the slot is provided with locating and locking means comprising a pyramidal taper complementary to the V-shaped notch in the blade. The end of the body portion remote from the shank, hereinafter referred to as the forward end, is formed as an enlarged truncated cone segment oriented with the taper directed toward the shank portion. An internally threaded collar slidably fits over the body portion and is prevented from sliding off said body portion by the enlarged cone segment. The collar is provided with an internal shoulder engageable with the tapered cone segment of the forward end of the body portion and serves as a stop. The threads of the collar engage the teeth of the saw blade, which preferably have no set at the trailing edge for a distance substantially equal to the depth of the slot in said body portion, such that tightening of the collar onto the blade draws the blade into the body portion until the V-shaped notch in the blade engages and is firmly seated on the pyramidal taper at the slot base. Tightening of the collar also urges the collar onto and against the tapered cone segment whereby the saw blade is clamped by the opposed halves of the body portion.

BRIEF DESCRIPTION OF THE DRAWINGS

In the accompanying drawings which illustrate the invention.

DETAILED DESCRIPTION OF THE INVENTION

Figure 1:
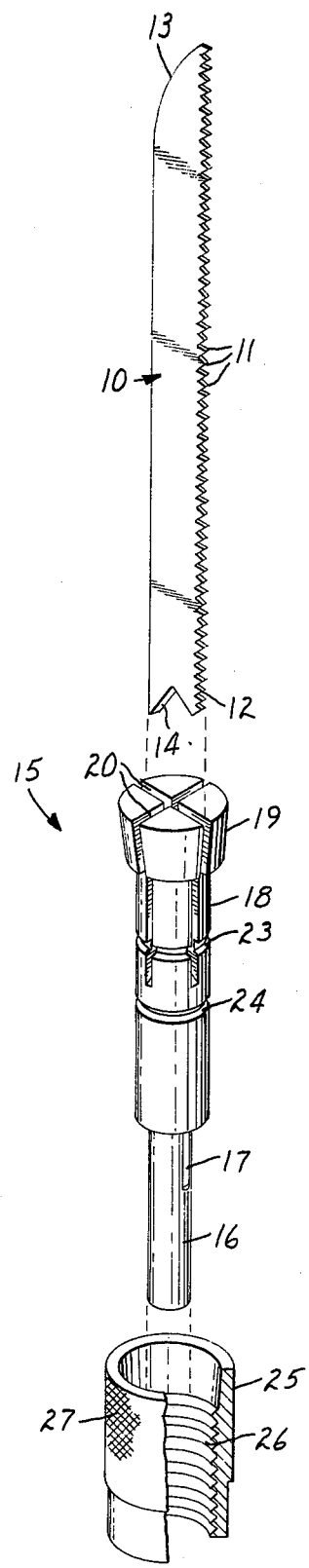
FIG. 1 is an exploded view of the saw blade fastening means of the present invention.
Figure 2:
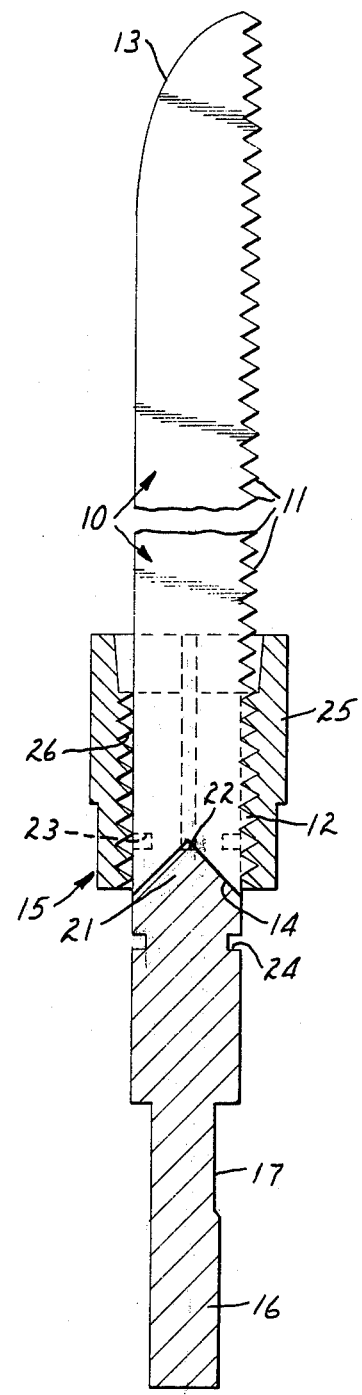
FIG. 2 is an enlarged sectional view through the saw blade fastening means in its assembled condition.

Referring particularly to the drawings, 10 denotes a surgical saw blade about 30 to 40 mils thick formed from 17-7 PH stainless steel stock and heat treated to 45–48 on the Rockwell C scale to withstand repeated steam sterilization. The blade is provided with sharp cutting teeth 11 along one edge thereof. The teeth 11 are normally set such that the outer edges of two adjoining teeth are inclined in opposite directions to provide for greater cutting efficiency. It is preferred that the teeth adjacent the trailing end 12 of the blade have no set for a distance equal to the length of the collar 25 on the chuck assembly 15. The other edge of blade 10 is curved adjacent the leading end 13 to form a smoothly pointed relatively blunt front or leading end. The blade may, of course, have a sharply pointed or a more rounded front or leading end as desired. The trailing end 12 of the blade 10 is provided with a V-shaped notch 14 with the apex of the "V" bisecting the midline of blade 10. The sides of the "V" are each inclined at an angle of 45° to the midline of the blade.

The depth of the V-shaped notch is about 0.075 inch and its width at the open end is about 0.15 inch.

The chuck assembly 15, formed of 416 stainless steel heat treated to 28–30 on the Rockwell C scale, comprises a shank portion 16 and a body portion 18. The shank portion 16 is formed as a cylindrical rod about 0.625 inch long and 0.155 inch in diameter with an approximately 0.25 inch long flat 17 provided thereon at its junction with the body portion 18 for locking engagement by a set-screw on the surgical instrument (not shown) into which the shank portion 16 is inserted.

The body portion 18 is also a cylindrical rodlike member having a length of about 1.05 inch and a diameter of 0.26 inch. The forward end 19 is in the form of an enlarged truncated cone segment tapering toward the shank portion of the body. As will be clearly seen in FIG. 1, body portion 18 is axially slotted for approximately half its length by slots 20 which are perpendicular to each other and have a width sufficient to freely accept saw blade 10 therewithin. The base of the slots 20 terminates in a pyramid 21 located such that the apex 22 is at the point of intersection of the slots 20 and is directed toward the open end of said slots. The sides of the pyramid 21 are inclined at an angle of 45° and thus are complementary to the V-shaped notch 14 in the trailing end 12 of blade 10.

Body portion 18 is transversely circumferentially grooved at a point substantially at the apex 22 of the pyramid 21. This transverse groove 23, formed by removing stock from the body portion, makes it possible to more easily compress the segmented forward end 19 when pressure is applied circumferentially to the segments by collar 25.

Body portion 18 is provided with a second transverse circumferential groove 24 at a point spaced from the truncated cone segment a distance sufficient to permit collar 25 to be loosely retained on body portion 18 by a retaining ring (not shown) fitting within groove 24.

Collar 25, formed from 440C stainless steel heat treated to 58–60 on the Rockwell C scale, is provided with internal threads 26 whose lands and grooves engage the lands and grooves of the teeth 11 of blade 10. In order to function effectively and permit repeated fastening cycles under use conditions, it has been found that collar 25 should be formed of a harder alloy than saw blade 10. Tests have shown that collars formed of materials of equivalent or lesser hardness than that of the saw blades could not be readily unfastened without the use of an auxiliary tool while those which were fabricated from harder materials performed without incident in the intended manner through repeated cycles. The exterior surface of collar 25 is knurled or otherwise patterned to provide a slip resistant gripping surface 27.

In a typical surgical procedure involving sectioning of bone, the surgeon would utilize a surgical saw powered by a hand-held air driver unit. Attached to the air driver, as an interchangeable accessory attachment, is a reciprocating saw attachment which translates the normal rotational motion of the air driver to the reciprocating motion required for sawing through bone. These attachments produce about 20,000 reciprocations per minute with a stroke of about 0.10 inch.

The surgical saw blade fastening means of the present invention would be securely fastened onto the reciprocating saw attachment by inserting shank 16 of chuck assembly 15 into a socket provided and tightening a set-screw onto the flat 17, in the usual manner.

With collar 25 loosely retained on body portion 18 of chuck assembly 15, a saw blade 10 is inserted into one of the axial slots 20 until the first of teeth 11 contacts the first thread 26 of collar 25. At this point tightening collar 25 by grasping same by the slip resistant gripping surface 27 and turning collar 25 to the right will cause blade 10 to be pulled further into slot 20 until V-shaped notch 14 is firmly seated on pyramid 21. At about the same time, collar 25 would be pulled forwardly onto truncated cone segment 19 thereby compressing the body portions on either side of slot 20 onto saw blade 10 to firmly clamp the saw blade 10 in position.

During such surgical procedures, it is frequently necessary to change saw blades or the position thereof in the chuck assembly. In such event, the above-noted procedure for inserting a surgical saw blade 10 is simply reversed and the position of the blade can then be changed to any of three other positions or a new blade inserted, all without the use of any additional hand tools as would be required for a conventional prior art saw blade having a shank brazed to the blade itself and where the shank is held firmly in place by a set-screw.

While the surgical saw blade fastening means of the present invention has been described herein as having certain shapes and dimensions and being formed of specific materials, it is to be understood that such recitations are exemplary and various modifications are possible and are contemplated. For example, surgical saw blades are presently offered in off-set configurations and in different lengths and thicknesses and these variants are contemplated. Similarly, other stainless steels and alloys which can withstand repeated steam sterilization cycles can be utilized. Also, although the chuck assembly 15 has been described as having two axial slots 20 intersecting at right angles so that the saw blade can be positioned in any of four positions at 90° intervals, other slot arrangements can be utilized to provide for other positioning options.

I claim:

1. A surgical saw blade fastening means comprising in combination:
   a surgical saw blade member having a plurality of cutting teeth along one edge of said saw blade member,
      the other edge of said saw blade member being smooth and sloped adjacent one end to intersect the toothed edge of said saw blade member.
      the other end of said saw blade member having a locating and locking means for securely holding said saw blade member in position,
   a chuck assembly having a shank portion for attachment to a surgical instrument,
      a body portion having at least one axial slot therein of a width sufficient to accept said saw blade member therewithin,
         the base of said slot having a locating and locking means complementary to the locating and locking means on said saw blade member, and
      an internally threaded collar carried on said body portion,
         the lands and grooves of the threads of said internally threaded collar being adapted to engage the lands and grooves of the teeth of said saw blade member thereby firmly engaging the locating and locking means of said saw blade member and said body portion and clampingly compressing the body portions on either side of said axial slot against said saw blade member.

2. A surgical saw blade fastening means according to claim 1 wherein the body portion of said chuck assembly has two axial slots therein of a width sufficient to accept said saw blade member therewithin, said slots intersecting at right angles.

3. A surgical saw blade fastening means according to claim 2 wherein the locating and locking means for securely holding said saw blade member in position comprises a V-shaped notch bisecting the midline of said blade member and the locating and locking means at the base of the axial slots in said body portion comprises a pyramid complementary to the V-shaped notch in said saw blade member.

4. A surgical saw blade fastening means according to claim 3 wherein the cutting teeth of said surgical saw blade member have no set at the trailing edge for a distance substantially equal to the depth of the axial slots in said body portion of said chuck assembly.

5. A surgical saw blade fastening means according to claim 4 wherein the internally threaded collar is formed of a harder material than the material of said saw blade.

* * * * *